(12) United States Patent
Burk et al.

(10) Patent No.: US 6,841,499 B1
(45) Date of Patent: Jan. 11, 2005

(54) SUPPORTED FERROCENE-BASED CATALYSTS FOR SELECTIVE ALDEHYDE HYDROGENATION

(75) Inventors: Mark Joseph Burk, Santa Clara, CA (US); Arne Gerlach, Cambridge (GB)

(73) Assignee: Chirotech Technology Limited, Cambridge (GB)

( * ) Notice: Subject to any disclaimer, the term of this patent is extended or adjusted under 35 U.S.C. 154(b) by 626 days.

(21) Appl. No.: 09/700,821

(22) PCT Filed: Oct. 6, 2000

(86) PCT No.: PCT/GB00/03851

§ 371 (c)(1),
(2), (4) Date: Nov. 20, 2000

(87) PCT Pub. No.: WO01/26807

PCT Pub. Date: Apr. 19, 2001

(30) Foreign Application Priority Data

Oct. 8, 1999 (GB) ............................................. 9923952

(51) Int. Cl.$^7$ ............................ B01J 31/16; B01J 31/24; B01J 31/28; C07C 29/14; C07C 29/114
(52) U.S. Cl. ..................... 502/117; 502/152; 502/166; 502/213; 502/208; 502/325; 502/87; 568/878; 568/880; 568/881; 568/883; 568/885
(58) Field of Search ................................ 502/117, 150, 502/152, 154, 166, 213, 208, 325, 326, 85, 87; 568/420, 878, 880, 881, 883, 885

(56) References Cited

U.S. PATENT DOCUMENTS

| | | | |
|---|---|---|---|
| 5,783,715 A | | 7/1998 | Pugin ........................... 556/11 |
| 5,817,850 A | * | 10/1998 | Pastor et al. ................... 556/14 |
| 6,172,249 B1 | * | 1/2001 | Berens et al. .................. 556/14 |
| 6,525,210 B1 | * | 2/2003 | Zhang et al. .................. 556/21 |
| 6,583,305 B1 | * | 6/2003 | Reetz et al. ................... 556/14 |

FOREIGN PATENT DOCUMENTS

WO 9828074 12/1997

OTHER PUBLICATIONS

Augustine, Robert, Setrak Tanielyan, Stephen Anderson and Hong Yang (1999) "A new technique for anchoring homogeneous catalysts" *Chem. Commun.*, p. 1257–1258. (no month).

Tani, Kazuhide et al. (1982) "Rh(I) Complexes Containing Fully Alkylated Mono–And Diphosphine Ligands As Highly Active Hydrogenation Catalysts For Carbonyl Compounds" *Chemistry Letters* pp 261–264, The Chemical Society of Japan. (no month).

Burk, Mark J., T. Gregory P. Harper, Jeffrey R. Lee, Christopher Kalberg (Jul. 11, 1994) "Efficient Rhodium–Catalyzed Hydrogenation of Aldehydes and Ketones" *134a Tetrahedron Letters* 35(28):4963–4966. (no month).

* cited by examiner

*Primary Examiner*—Michael La Villa
(74) *Attorney, Agent, or Firm*—James Drake

(57) ABSTRACT

A supported catalyst comprises a cationic rhodium(I) complex of the formula

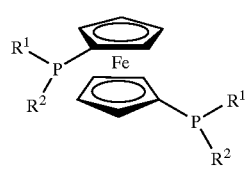

wherein $R^1$ and $R^2$ are the same or different hydrocarbon groups of up to 30 C atoms, or $R^1$ and $R^2$ are linked to form a ring, and a heterogeneous support medium that provides anionic binding sites.

Such a complex is particularly useful as a catalyst in a process of hydrogenating an aldehyde to produce the corresponding primary alcohol.

6 Claims, No Drawings

SUPPORTED FERROCENE-BASED CATALYSTS FOR SELECTIVE ALDEHYDE HYDROGENATION

FIELD OF THE INVENTION

This invention relates to a supported catalyst and to its use, e.g. in the efficient and selective hydrogenation of aldehydes to alcohols.

BACKGROUND OF THE INVENTION

Both homogeneous and heterogeneous catalysts are known, as are their respective advantages and disadvantages. One way of combining the features of both is to immobilise or tether a homogeneous catalyst to a polymeric or inorganic solid support. Arr undesirable aspect of this strategy is that the heterogenised ligand systems often are very tedious and/or expensive to prepare. Another problem is that polymer-supported homogeneous catalysts frequently have reduced catalytic activities and selectivities relative to the unsupported homogeneous analogues. Upon attempted reuse, the activities and selectivities of these catalysts are often reduced further. Finally, many immobilised homogeneous catalysts suffer from a high degree of metal loss from the support (leaching) during use; see, for example, Lindner, et al, *Angew. Chemie Int. Ed.* 1999, 38, 2155.

Aldehyde reduction often is a desirable step in obtaining valuable alcohol products from inexpensive starting materials (e.g., alkenes, hydrogen and carbon monoxide in the case of hydroformylation). Despite the importance of aldehyde reduction in organic chemistry, surprisingly few generally applicable manufacturing methods are available for this transformation. Hydride reducing agents (e.g. $LiAlH_4$ or $NABH_4$) are widely used, but are moisture-sensitive reagents that are not economically attractive for commercial procedures since they are employed in stoichiometric quantities. Moreover, their use requires tedious work-up procedures and generates substantial quantities of waste (boron or aluminium salts).

Numerous heterogeneous catalysts, such as $PtO_2$, Raney Ni, and Pd/C, can catalyse the reduction of specific aldehydes. However, heterogeneous catalysts are often intolerant of various organic groups such as divalent sulfides. Moreover, other sensitive groups such as nitro, oxime, ketone, aryl halide or benzyloxy, also are reduced. Another problem encountered when reducing aromatic aldehydes using heterogeneous catalysts is that the product may be further reduced to a methyl substituent. For example, heterogeneous hydrogenation of benzaldehyde often affords toluene.

Very few practical homogeneous systems efficiently catalyse aldehyde hydrogenation. Problems often encountered include low reaction rates and/or catalyst deactivation due to aldehyde decarbonylation processes.

The use of cationic rhodium catalysts for aldehyde hydrogenation has been reported by Tani et al, *Chem. Lett.* 1982, 261, and by Burk et al, *Tetrahedron Lett.* 1994, 35, 4963. Results suggest that the achievement of high efficiency in rhodium-catalysed aldehyde hydrogenation requires the use of electron-rich (dialkyl- or trialkyl-substituted) chelating phosphine ligands, but these tend to be very air-sensitive and are not suitable for industrial manufacture. Burk et al. describes an electron-rich, yet air-stable crystalline ligand, 1,1'-bis(diisopropylphosphino)ferrocene (DiPFc) 1 ($R^1=R^2=$ i-Pr). The homogeneous rhodium catalyst (DiPFc-Rh) also is stable to oxygen and has been shown to hydrogenate a limited set of aldehydes with high reaction rates.

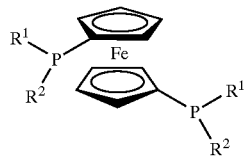

1

A new method of anchoring certain rhodium catalysts to solid supports has recently been described by Augustine et al, *Chem. Comm* 1999, 1257. This simple procedure involves treating a readily available solid material (silica, alumina, carbon, etc.) with a heteropolyacid such a phosphotungstic acid, followed by addition of an appropriate catalyst precursor complex. Immobilised catalysts formed in this fashion were reported to serve as active and reusable catalysts for alkene hydrogenation.

SUMMARY OF THE INVENTION

According to the present invention, an immobilised homogeneous catalyst is useful, inter alia, for the efficient and chemoselective hydrogenation of aldehydes. The catalyst system is based upon homogeneous rhodium complexes bearing phosphines of formula 1, wherein $R^1$ and $R^2$ are independently the same or different hydrocarbon substituents, e.g. alkyl, substituted alkyl, arylalkyl or aryl, of up to 30 C atoms, or $R^1$ and $R^2$ are linked to form a ring. Preferably, $R^1$ and $R^2$ are alkyl groups and more preferably identical alkyl groups. The solid support provides anionic binding sites.

The utility of the novel catalyst is surprising, for various reasons. Firstly, it was not evident that the complex could be supported. Secondly, its activity for aldehyde hydrogenation is good especially given the acidic nature of the support. Further, the immobilised hydrogenation catalyst can be effectively recovered and re-used.

DESCRIPTION OF THE INVENTION

Solid supports that are effective for use in the invention are those providing anionic binding sites. The support may or may not be modified with a heteropolyacid anchoring agent. The support medium is preferably an oxide such as alumina, silica, carbon, montmorillonite, etc., and is preferably modified with a heteropolyacid. The heteropolyacid is preferably of the Keggin type, e.g. phosphotungstic acid, phosphomolybdic acid or silicotungstic acid. Alternatively, an anionic exchange resin such as poly para-toluenesulfonic acid or Nafion in its acidic or anionic form may be used. For example, the support medium is a cation exchange resin containing sulphonic acid groups $—SO_3^-X^+$, wherein $X^+$ is a proton or any other exchangeable cation. A preferred cation exchange resin is a tetrafluoroethylene-perfluoro (vinyl ether sulfonate) copolymer.

Many different types of aldehydes, e.g. of formula RCHO, wherein R is an organic group up to 30 C atoms, may be hydrogenated to give $RCH_2OH$, using the novel catalyst The aldehyde substrate may possess a range of different functional groups that either inhibit or react with commonly employed heterogeneous catalysts. Due to the acidic nature of the supports used in the immobilisation of the homogeneous catalyst, a non-standard solvent mixture may be required. The use of an alcohol/water mixture, and particularly an isopropanol/water mixture, is preferred, so that the hydrogenation reaction proceeds to completion. In particular, acetal formation can be minimised or avoided. The immobilised catalyst system may be recovered by simple filtration and re-used in subsequent reactions.

In addition to the hydrogenation of aldehydes, a catalyst of the invention may also be used for hydrogenation of other unsaturated groups. For example, unsaturated functionality such as the carbon-carbon double bond of alkenes, the carbon-carbon triple bond of alkynes, the carbon-oxygen double bond of ketones and the carbon-nitrogen double bond of substrates such as N-acylhydrazones may be hydrogenated using these catalyst systems.

Some aldehydes are quite temperature-sensitive and decompose as the temperature is increased much above room temperature. In such cases, the ability to perform the hydrogenation at mild temperatures is vital. Increasing the temperature may increase the reaction rate, but the novel catalyst may be performed over a broad temperature range of −30° C. to +150° C. The preferred temperature is in the range 0° C. to 60° C.

Performing reactions under low pressure is often preferred for manufacturing due to the fact that high-pressure equipment is more costly to purchase and operate. An important advantage of this invention is that the catalyst can perform effectively under both high and low hydrogen pressures, e.g. over the range of 1 to 100 atmospheres (100–10000 kPa). Increasing the pressure may increase the reaction rates. The preferred pressure range will depend on the process being operated and the desired reaction rates.

Heterogenised rhodium catalyst systems bearing 1,1'-bis(dialkylphosphino)ferrocene ligands 1 may be prepared via various procedures. By way of representative example, an immobilised catalyst may be formed by mixing neutral alumina with phosphotungstic acid in methanol, followed by the addition of the catalyst precursor [(COD)Rh(DiPFc)]$^+$BF$_4^-$ (see Scheme 1). After allowing the mixture to stir for a specified period, the rhodium complex is completely absorbed onto the solid support. The tethered catalyst is then filtered, washed with methanol, and employed directly in catalysis. The mechanism of absorption and the exact nature of the tethered complex are unclear.

Scheme 1.

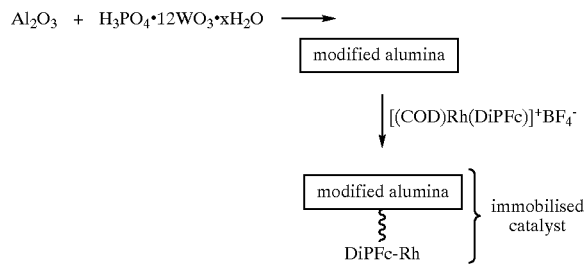

The DiPFc-Rh catalyst prepared as in Scheme 1 has been tested for effectiveness in the hydrogenation of a range of different multifunctional aldehydes. These studies were aimed at demonstrating the combined properties of high catalytic efficiency under mild conditions, selectivity in the reduction process, and tolerance of the catalyst to certain functionality. The robust nature of the catalyst system also was important. Moreover, comparisons have been made with commonly employed heterogeneous catalysts such as palladium on carbon, platinum oxide, and palladium on barium sulfate.

The following Examples illustrate the invention.

EXAMPLE 1

Preparation of [(DiPFc)Rh(COD)]X on Modified Silica

A solution of phosphotungstic acid (PTA, 288 mg, 0.1 mmol, 1.0 eq.) in 25 ml degassed methanol was added dropwise to a vigorously stirred (overhead stirrer was used to minimise grinding) suspension of 4.00 g silica (Silica gel 60 for flash chromatography (Fluka), particle size 0.035–0.070 mm (220–440 mesh ASTM, activity according to Brockmann and Schrodder: 2–3) in 30 ml of degassed methanol under nitrogen. The resulting mixture was stirred for 1 hour at room temperature. Subsequently, a solution of [(DiPFc)Rh(COD)]BF$_4$ (64 mg, 0.09 mmol, 0.9 eq.) in 10 ml degassed methanol was dripped to the vigorously stirred slurry of the activated silica. Stirring was continued for 4.5 hours at room temperature. After solvent evaporation the remaining solid was placed in a Soxhlet apparatus and continuously extracted with degassed methanol under nitrogen for 16 hours. The orange silica powder was isolated, dried and stored under nitrogen as a precaution. Yield: 3.64 g (86%).

The alumina supported DiPFc-Rh catalyst was prepared by an analogous protocol to that outlined above.

EXAMPLE 2

General Hydrogenation Procedure

All reactions were carried out in a 50 ml Parr microreactor modified with an injection septum and valve. The micro reactor was used in connection with a suitable glass liner. The solvent (2-propanol/water mixture, 1:1 v/v) was deoxygenated by bubbling nitrogen through it for 3 hours while stirring. The hydrogenation substrate and the immobilised catalyst were added to a 50 ml glass liner, which was then immediately placed in a 50 ml Parr pressure vessel. This was then sealed and purged with hydrogen (5 pressurisation (690 kPa)/release cycles). Degassed solvent (2-propanol/water; 1:1 v/v) was then added via cannula, the reactor purged again with hydrogen (5 pressurisation (690 kPa)/release cycles), charged to the initial hydrogen pressure (690 kPa) and vigorously stirred at a constant temperature (ambient temperature or heating bath). After an allocated period of time (hydrogen uptake was monitored) hydrogen pressure was released, and the reaction mixture was filtered (separation from the supported catalyst). The filtrate was then extracted several times with dichloromethane. The combined organic extracts were dried over sodium sulfate, filtered and evaporated. The product distribution of the crude product mixture was determined by $^1$H-NMR spectroscopy and was compared with authentic samples of all products. In cases where the formation of water-soluble or volatile products was likely, the hydrogenation mixture also was analysed via HPLC prior to extractive work-up.

Thus, experiments were performed under a standard set of mild reaction conditions: conversion to product=100%, hydrogen pressure=690 kPa, temperature=20° C., reaction time=16 h, mol aldehyde/mol Rh=300–500 (based upon analysis of Rh content), concentration=0.1 M, solvent: 2-propanol/water (1:1 v/v). Analytical procedures and results are given in Table 1.

The results show that the catalyst was robust and would operate effectively under very mild reaction conditions. This is demonstrated by the fact that all experiments listed in Table 1 were conducted using catalyst that was stored under an atmosphere of air for a period of ten months. This immobilised homogeneous catalyst allowed complete hydrogenation of each aldehyde listed to afford exclusively the desired alcohol product in high yield. The results further reveal that aldehydes bearing either alkyl substituents (R=alkyl) or aromatic substituents (R=aryl) may be reduced with equal facility. Functional groups that are reduced by most common heterogeneous catalysts, including aryl halide, nitro, and benzyloxy, were not reduced.

In contrast, common heterogeneous catalysts invariably yielded mixtures of products due to low chemoselectivity in reduction of the aldehyde carbonyl group (substrates 7–9, 13). In all cases using the heterogeneous catalysts, milder than normal reaction conditions were employed in an effort to achieve some level of selectivity in the reduction process.

This strategy provided the best advantage to the heterogeneous catalyst, but resulted in incomplete conversion of starting aldehyde in some cases. In all such cases, driving the reactions further to allow complete conversion of substrate led to lower selectivities.

Importantly, the novel catalyst displayed broad tolerance to various organic functionalities, including sulphur-containing groups, with no apparent diminution of catalytic rates. Sulphur functionality is notoriously detrimental to most heterogeneous catalysts, leading to serious levels of catalyst inhibition. This point was amply demonstrated in experiments 10–13. Of particular note is the successful hydrogenation of substrates 10 and 12, which contain non-aromatic sulfide groups.

In addition to a catalyst with an alumina solid support, identical results were achieved using a DiPFc-Rh catalyst anchored to silica in the fashion described above in Scheme 1 (see hydrogenation results involving substrate 12). The use of a silica support offers significant practical advantages since this immobilised catalyst system is more readily handled and removed from the reaction mixtures.

One advantage of an immobilised catalyst is the potential to remove it completely from the reaction mixture through filtration, and also to reuse the catalyst in subsequent processes. This is demonstrated by performing 4 successive hydrogenations involving 2-thiophene carboxaldehyde (substrate 11). This particular aldehyde bears sulfur functionality, which should test the robustness of the immobilised catalyst in the presence of potential coordinating groups. In each case the hydrogenation was performed under conditions described in Table 1. After allowing the reaction to stir for 6 h (hydrogen uptake was monitored), a small sample was removed, and complete conversion to alcohol product was confirmed by $^1$H NMR spectroscopy. The entire solution phase containing the product then was removed by syringe, the catalyst was washed twice with fresh solvent, and a subsequent aliquot of hydrogenation substrate in 2-propanol/water was added. The immobilised catalyst was used successfully for four catalytic cycles, and complete conversion to the corresponding alcohol product was observed after each run. No reduction of catalytic activity was noted over the four cycles.

TABLE 1

Selective Aldehyde Hydrogenations

| Substrate | Catalyst[a] | Product Distribution[b] | | | |
|---|---|---|---|---|---|
| n-C₄H₉-CHO | | n-C₄H₉-CHO | | n-C₄H₉-CH₂OH | |
| 6 | DiPFc-Rh on alumina | n.d.[c] | | 100% | |
| 4-Br-C₆H₄-CHO | | 4-Br-C₆H₄-CHO | 4-Br-C₆H₄-CH₂OH | C₆H₅-CHO | C₆H₆ |
| 7 | DiPFc-Rh on alumina | n.d. | 100% | n.d. | n.d.[e] |
|   | dppb-Rh on silica | 93% | 7% | n.d. | n.d. |
|   | Platinum oxide | 1% | 90% | <1% | 8% |
|   | Pd on carbon | 80% | n.d. | 20% | n.d.[e] |
|   | Pd on carbon[d] | n.d. | n.d. | n.d. | 100%[e] |
|   | Pd on barium sulfate [f] | 85% | n.d. | 15% | n.d.[e] |
| 4-NO₂-C₆H₄-CHO | | 4-NO₂-C₆H₄-CHO | 4-NO₂-C₆H₄-CH₂OH | nitro-reduced products | |
| 8 | DiPFc-Rh on alumina | n.d. | 100% | n.d. | |
|   | Pd on carbon | 58% | 0% | 42% | |
| 4-OBn-C₆H₄-CHO | | 4-OBn-C₆H₄-CHO | 4-OBn-C₆H₄-CH₂OH | 4-OH-C₆H₄-CHO | 4-OH-C₆H₄-CH₂OH |
| 9 | DIPFc-Rh on alumina | n.d. | 100% | n.d. | n.d. |
|   | Pd on carbon | n.d. | n.d. | 40% | 60% |

TABLE 1-continued

Selective Aldehyde Hydrogenations

| | Catalyst[a] | Product Distribution[b] | |
|---|---|---|---|
| | | ~S~~/~~CHO[h] | ~S~~/~~CHO | ~S~~/~~CH₂OH |
| 10 | DiPFc-Rh on alumina | n.d. | 100% |
| | Pd on carbon[i] | 100% | n.d. |
| | Platinum oxide[l] | >98% | <2% |
| | | (2-thienyl)-CHO | (2-thienyl)-CHO | (2-thienyl)-CH₂OH |
| 11 | DiPFc-Rh on alumina | n.d. | 100% |
| | Pd on carbon[j] | 92% | 8% |
| | | 4-SMe-C₆H₄-CHO | 4-SMe-C₆H₄-CHO | 4-SMe-C₆H₄-CH₂OH |
| 12 | DiPFc-Rh on alumina | n.d. | 100% |
| | DiPFc-Rh on silica | n.d. | 100% |
| | DiPFc-Rh on silica[j] | n.d. | 100% |
| | DiPFc-Rh on silica[k] | 69% | 31% |
| | dppb-Rh on silica | 100% | 0% |
| | Platinum oxide[l] | 3% | 97% |
| | Pd on carbon[i] | 95% | 5% |

| | Catalyst[a] | Product Distribution[b] | | |
|---|---|---|---|---|
| | | Br-(thienyl)-CHO | Br-(thienyl)-CHO | Br-(thienyl)-CH₂OH | (thienyl)-CHO |
| 13 | DiPFc-Rh on alumina | 40% | 60% | n.d. |
| | Pd on carbon | 17% | n.d. | 83% |

[a] Hydrogenation conditions for DiPFc-Rh on alumina or silica: 100 psi hydrogen, S/C>300, 0.1 molar in 2-propanol-water (1:1), room temperature, overnight; conditions for dppb-Rh on silica: 100 psi hydrogen, S/C>200, 0.1 molar in 2-propanol-water (1:1), room temperature, overnight; conditions for platinum oxide: 1 bar hydrogen, 5 mg catalyst per mmol substrate, 0.1 molar 2-propanol-water (1:1), room temperature, 30 mins; conditions for palladium on carbon (10%): 1 bar hydrogen, 5 mg catalyst per mmol substrate, 0.1 molar in 2-propanol-water (1:1), room temperature, 30 mins. [b] Determined by $^1$H-NMR analysis after extraction of the crude reaction mixture with dichloromethane, drying (sodium sulfate) and evaporation. [c] Not detected by $^1$H-NMR, GC or HPLC. [d] Reaction conditions: 100 psi hydrogen, 10 mg palladium on carbon (10%) per mmol substrate, room temperature, 1 hour. [e] Determined by HPLC analysis of the crude reaction mixture. [f] Reaction conditions: 1 bar hydrogen, 5 mg palladium on barium sulfate (5%) per mmol substrate, room temperature, 30 mins. [g] Detected by HPLC analysis of the crude reaction mixture. [h] Purchased from Fluka as a technical mixture of various amounts of monomers and oligomers. [i] Reaction conditions: 100 psi hydrogen, 10 mg palladium on carbon (10%) per mmol substrate, room temperature, 16 hours. [j] Reaction conditions: 100 psi hydrogen, S/C>500, 60° C., 20 hours. [k] Reaction conditions: 100 psi hydrogen, S/C>1000, 60° C., 24 hours. [l] Reaction conditions: 100 psi hydrogen, 10 mg platinum oxide per mmol substrate, room temperature, 16 hours.

What is claimed is:

1. A supported catalyst suitable for the hydrogenation of aldehyde, and alkene or an alkyne comprising a cationic rhodium(I) complex of a diphosphine ligand of the formula

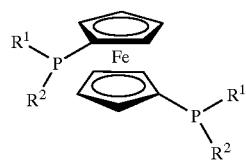

1 wherein $R^1$ and $R^2$ are the same or different hydrocarbon groups of up to 30 carbon atoms or $R^1$ and $R^2$ are linked to form a ring, and a heterogeneous support medium comprising a cation exchange resin containing sulphonic acid groups —$SO_3X^+$ wherein $X^+$ is a proton or any other exchangeable cation.

2. The catalyst according to claim 1, wherein the cation exchange resin is a tetrafluoroethylene-perfluoro(vinyl ether sulfonate) copolymer.

3. The catalyst according to claim 1, wherein $R^1$ and $R^2$ are each an alkyl group.

4. The catalyst according to claim 3, wherein $R^1=R^2=$i-Pr.

5. A process of hydrogenating an aldehyde to produce the corresponding primary alcohol wherein said process utilizes a supported catalyst comprising a cationic rhodium (I) complex of a diphosphine ligand of the formula

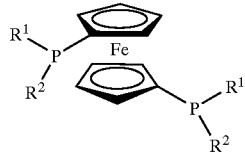

wherein $R^1$ and $R^2$ are the same or different hydrocarbon groups of up to 30 carbon atoms, or $R^1$ and $R^2$ are linked to form a ring, and a heterogeneous support medium that provides anionic binding sites.

6. The process according to claim 5, wherein substrate conversion of at least 90% is effected, and wherein the aldehyde contains at least one sulfide group that is retained in the product, and wherein the process is carried out in a mixture of water and an alcohol.

* * * * *